US006479045B2

(12) United States Patent
Bologna et al.

(10) Patent No.: US 6,479,045 B2
(45) Date of Patent: Nov. 12, 2002

(54) VAGINAL PH BUFFERING FOR PREVENTING MISCARRIAGE AND PREMATURE LABOR, BY TREATING OR PREVENTING BACTERIAL VAGINOSIS

(75) Inventors: William J. Bologna, Paris (FR); Howard L. Levine, Oceanside, NY (US)

(73) Assignee: Columbia Laboratories, Inc., Rockville Centre, NY (US)

( * ) Notice: Subject to any disclaimer, the term of this patent is extended or adjusted under 35 U.S.C. 154(b) by 0 days.

(21) Appl. No.: 09/748,753

(22) Filed: Dec. 21, 2000

(65) Prior Publication Data

US 2001/0031251 A1 Oct. 18, 2001

Related U.S. Application Data

(60) Provisional application No. 60/171,454, filed on Dec. 22, 1999.

(51) Int. Cl.$^7$ ............................................. A61K 31/74
(52) U.S. Cl. .............................. 424/78.08; 424/78.17; 424/451; 424/464; 424/422; 424/430; 424/436; 424/434; 424/400
(58) Field of Search ................................. 424/430, 422, 424/78.02, 78.07, 78.08, 78.17, 451, 464, 436, 434, 400; 514/772.3, 773.6

(56) References Cited

U.S. PATENT DOCUMENTS

| | | | |
|---|---|---|---|
| 4,615,697 A | 10/1986 | Robinson | 604/890 |
| 4,795,436 A | 1/1989 | Robinson | 424/422 |
| 4,983,392 A | 1/1991 | Robinson | 424/427 |
| 5,225,196 A | 7/1993 | Robinson | 424/427 |
| 5,474,768 A | 12/1995 | Robinson | 424/78.31 |
| 5,543,150 A | 8/1996 | Bologna et al. | 424/430 |
| 5,667,492 A | 9/1997 | Bologna et al. | 604/57 |
| 5,968,500 A | 10/1999 | Robinson | 424/78.08 |
| 6,017,521 A | 1/2000 | Robinson et al. | 424/78.02 |
| 6,126,959 A | 10/2000 | Levine et al. | 424/434 |

FOREIGN PATENT DOCUMENTS

| | | |
|---|---|---|
| WO | WO 99/13862 A2 * | 3/1999 |
| ZA | 98/08328 | 5/1999 |

OTHER PUBLICATIONS

Kent, H.L., "Epidemiology of Vaginitis," *American Journal of Obstetrics and Gynecology*, vol. 165, No. 4, Oct. 1991, pp. 1168–1176.

Kurki, T., et al., "Bacterial Vaginosis in Early Pregnancy and Pregnancy Outcome," *Obstetrics and Gynecology*, vol. 80, No. 2, Aug. 1992, pp. 173–177.

Riduan, J.M., et al., "Bacterial vaginosis and prematurity in Indonesia: Association in early and late pregnancy," *American Journal of Obstetrics and Gynecology*, vol. 169, No. 1, Jul. 1993, pp. 175–178.

Hay, P.E., et al., "Abnormal bacterial colonization of the genital tract and subsequent preterm delivery and late miscarriage," *British Medical Journal*, vol. 308, No. 6924, Jan. 1994, pp. 295–298.

McGregor, J.A., et al., "Prevention of premature birth by screening and treatment for common genital tract infections: Results of a prospective controlled evaluation," *American Journal of Obstetrics and Gynecology*, vol. 173, No. 1, Jul. 1995, pp. 157–167.

Hillier, S.L., et al., "Association between Bacterial Vaginosis and Preterm Delivery of a Low–Birth–Weight Infant," *The New England Journal of Medicine*, vol. 333, No. 26, Dec. 1995, pp. 1737–1742.

Watts, D.H., et al., "Bacterial Vaginosis as a Risk Factor for Post–Cesarean Endometriosis," *Obstetrics and Gynecology*, vol. 75, No. 1, Jan. 1990, pp. 52–58.

Ralph, S.G., et al., "Influence of bacterial vaginosis on conception and miscarriage in the first trimester: cohort study," *British Medical Journal*, vol. 319, No. 7204, Jul. 1999, pp. 220–223.

Rosenstein, I.J., et al., "Relationship between Hydrogen Peroxide–Producing Strains of Lactobacilli and Vaginosis–Associated Bacterial Species in Pregnant Women," *European Journal of Clinical Microbiology & Infectious Diseases*, vol. 16, No. 7, Jul. 1997, pp. 517–522.

Gardner, H.L., Dukes, D.C., "Haemophilus Vaginalis Vaginitis. A Newly Defined Specific Infection Previously Classified 'Nonspecific' Vaginitis", *American Journal of Obstetrics and Gynecology*, vol. 69, No. 5, May 1955, 962–76.

Amsel, R., et al., "Nonspecific Vaginitis. Diagnostic Criteria and Microbial and Epidemiologic Associations," *The American Journal of Medicine*, vol. 74, No. 1, Jan. 1983, pp. 14–22.

Aral, S.O., et al., "Self–reported Pelvic Inflammatory Disease in the United States, 1988," *The Journal of the American Medical Association*, vol. 266, No. 18, Nov. 1991, pp. 2570–2573.

Wolner–Hanssen, P., et al., "Association Between Vaginal Douching and Acute Pelvic Inflammatory Disease," *The Journal of the American Medical Association*, vol. 263, No. 14, Apr. 1990, pp. 1936–1941.

(List continued on next page.)

Primary Examiner—Thurman K. Page
Assistant Examiner—Liliana Di Nola-Baron
(74) Attorney, Agent, or Firm—Winston & Strawn

(57) ABSTRACT

The present invention concerns compositions and methods for preventing miscarriage and premature labor, and for treating and preventing Bacterial Vaginosis using a pH-buffering polymer. The present invention further concerns formulating such a composition or method in such a way as to provide therapeutically sufficient levels of the composition to a patient in need thereof.

18 Claims, No Drawings

OTHER PUBLICATIONS

Scholes, D., et al., "Vaginal Douching as a Risk Factor for Acute Pelvic Inflammaotory Disease," *Obstetrics and Gynecology*, vol. 81, No. 4, Apr. 1993, pp. 601–606.

Chow, W–H, et al., "Vaginal douching as a potential risk factor for tubal ectopic pregnancy," *American Journal of Obstetrics and Gynecology*, vol. 153, No. 7, Dec. 1985, pp. 727–729.

Chow, J.M., et al., "The Association Between *Chlamydia trachomatis* and Ectopic Pregnancy," *The Journal of the American Medical Association*, vol. 263, No. 23, Jun. 1990, pp. 3164–3167.

Daling, J.R., et al., "Vaginal Douching and the Risk of Tubal Pregnancy," *Epidemiology*, vol. 2, No. 1, Jan. 1991, pp. 40–48.

Kendrick, J.S., et al., "Vaginal douching and the risk of ectopic pregnancy among black women," *American Journal of Obstetrics and Gynecology*, vol. 176, No. 5, May 1997, pp. 991–997.

Baird, D.D., et al., "Vaginal Douching and Reduced Fertility," *American Journal of Public Health*, vol. 86, No. 6, Jun. 1996, pp. 844–850.

Larsson, P–G, "Treatments for bacterial vaginosis: an update on the expected cure rate," *Int'l J. of STD & AIDS*, vol. 8, Supp. 1, 1997, pp. 35–36.

Larsson, P.G., et al., "Treatment of Bacterial Vaginosis in Women with Vaginal Bleeding Complications or Discharge and Harboring *Mobiluncus*," *Gynecologic and Obstetric Investigation*, vol. 29, May 1990, pp. 296–300.

*The United States Pharmacopeia*, 1995 edition, United States Pharmacopeia Convention, Inc., Rockville, Maryland, pp. 1240–1241.

Robinson, J.R., Leung, S–H., Park, H., "Mechanisms of Adhesion of Swelling Insoluble Polymers to Mucin Epithelial Surfaces," Proceedings of the $12^{th}$ International Symposium on Controlled Release of Bioactive Materials, Jul. 1985, Geneva, Switzerland.

Park, H., Robinson, J.R., "Physico–Chemical Properties of Water Insoluble Polymers Important to Mucin/Epithelial Adhesion," *Journal of Controlled Release*, vol. 2, 1985, pp. 47–57.

March, D., Nakamura, R., "Evaluation of the Duration of Effect of a Bioadhesive Vaginal Moisturizing Gel on Vaginal pH," Abstract presented at the $7^{th}$ International Congress on the Menopause, Jun. 20–24, 1993, Stockholm, Sweden.

Gelfand, M., Wendman, E., "Treating Vaginal Dryness in Breast Cancer Patients: Results of Applying a Polycarbophil Moisturizing Gel," *Journal of Women's Health*, vol. 3, No. 6, Dec. 1994, pp. 427–434.

* cited by examiner

VAGINAL PH BUFFERING FOR PREVENTING MISCARRIAGE AND PREMATURE LABOR, BY TREATING OR PREVENTING BACTERIAL VAGINOSIS

This application claims the benefit of United States Provisional Patent Application No. 60/171,454, filed Dec. 22, 1999.

FIELD OF THE INVENTION

This invention relates to compositions and methods for preventing miscarriage and premature labor, and for treating and preventing Bacterial Vaginosis.

BACKGROUND OF THE INVENTION

Bacterial Vaginosis (BV) is broadly defined as a shift in vaginal ecology from a normal lactobacillus dominated flora to a profuse mixed microbial flora consisting of facultative and anaerobic organisms. An ancient condition first described by Hippocrates, BV is now the most common vaginal disorder in women of reproductive age, Kent, H. L., *Epidemiology of vaginitis, A. J Obstet. Gynecol.* 1991 165:1168, afflicting 15 to 20 percent of all women at any given time. In the United States, BV is the leading variety of vaginal infection, affecting a broader spectrum of women than gonorrhea. Id.

A primary medical significance of BV is its impact upon the quality of fetal implantation and its potential to induce premature labor, resulting in low birth-weight infants. BV during pregnancy also has been associated with an increased risk of late miscarriage. Kurki, T, et al., *Bacterial vaginosis in early pregnancy and pregnancy outcome, Obstet. Gynecol.* 1992, 80:173–77; Riduan, J. M. et al., *Bacterial vaginosis and prematurity in Indonesia: Association in early and late pregnancy, Am. J. Obstet. Gynecol.* 1993, 169:175–78; Hay, P. E., et al., *Abnormal bacterial colonization of the genital tract and subsequent preterm delivery and late miscarriage, BMJ* 1994, 308:295–98; McGregor, J. A., et al., *Prevention of premature birth by screening and treatment for common genital tract infections results of a prospective controlled evaluation, Am J. Obstet. Gynecol.* 1995, 173:157–67, Hillier, S. L., et al., *Association between bacterial vaginosis and preterm delivery of a low birth-weight infant, N. Engl. J. Med.* 1995, 333,1737–42; Watts, D. H., et al., *Bacterial vaginosis as a risk factor for post-cesarean endometriosis, Obstet. Gynecol.* 1990, 75,52–58.

The prevalence of BV in pregnant women is reported to be about 13 to 31 percent. Kurki, T, et al., *Bacterial vaginosis in early pregnancy and pregnancy outcome, Obstet. Gynecol.* 1992, 80,173–77. Riduan, J. M. et al., *Bacterial vaginosis and prematurity in Indonesia: Association in early and late pregnancy, Am. J. Obstet. Gynecol.* 1993, 169:175–78; Hay, P. E., et al., *Abnormal bacterial colonization of the genital tract and subsequent preterm delivery and late miscarriage, BMJ* 1994, 308:295–98; McGregor, J. A., et al., *Prevention of premature birth by screening and treatment for common genital tract infections: results of a prospective controlled evaluation, Am J. Obstet. Gynecol.* 1995, 173:157–67; Hillier, S. L., et al., *Association between bacterial vaginosis and preterm delivery of a low birth-weight infant, N. Engl. J. Med.* 1995, 333:1737–42. In women undergoing in-vitro fertilization, BV is associated with increased risk of miscarriage in the first trimester. Ralph, S. G. et al., *Influence of bacterial vaginosis on conception and miscarriage in the first trimester. Cohort study, BMJ* 1999, 319,220–3. Even if the fetus of a woman suffering from BV does survive the first and second trimester, however, the mother still faces an increased risk of premature labor with a higher probability of a low birth-weight infant and the attendant problems and consequences.

The exact pathogenesis and medical classification (e.g., disease or condition) of BV is uncertain. Under normal conditions, lactobacillus bacteria are predominant in the vagina and are believed to regulate the growth of other vaginal flora by producing hydrogen peroxide ($H_2O_2$). In women with BV, however, normal vaginal lactobacilli are replaced by an overgrowth of Gardnerella vaginalis, anaerobes, and mycoplasmas, with a concomitant decrease in lactobacilli. Thus, while $H_2O_2$-producing lactobacilli can be found in women with BV, these may not be enough to overcome the onslaught of multiplying endogenous bacteria that in turn force out lactobacilli as the dominant member of the flora. Rosenstein, I. J., et al, *Relationship between hydrogen peroxide producing strains of lactobacilli and vaginosis associated with bacterial species in pregnant women, Eur. J. Clin. Microbial. Infect. Dis.* 1997, 6:517–22.

The diagnostic signs of BV include increased vaginal discharge, production of "fishy" smelling amines, vaginal pH above 4.7, and presence of clue cells within a mixed flora. These were first described by Gardner and Dukes in 1955, Gardner H. L., Dukes, D. C., *Haemophilus vaginalis vaginitis. A newly defined specific infection previously classified "nonspecific vaginitis, Am. J. Obstet. Gynecol.* 1955, 69:962–76, and defined as the basic diagnostic criteria for BV in 1983. Amsel, R., et al., *Nonspecific Vaginitis. Diagnostic criteria and microbial and epidemiologic associations, Am. J. Med.* 1983, 74:14–22.

A woman may or may not experience the symptoms of BV; many women, however, complain of foul, fishy odor and excessive vaginal discharge that stains undergarments. The odor is particularly prominent for 24 hours after unprotected intercourse because of the high pH (7.8–8.2) and extensive buffering capacity of semen. Women who have recently acquired BV may be more aware of abnormal odor and discharge than a woman who has had the problem for months or even years. Often women first recognize that they had a problem after appropriate therapy. Further, many healthy women consider the symptoms of BV to indicate a lack of proper hygiene, rather than a medical problem.

In the United States, the unpleasant odor and discharge associated with BV causes many women to seek diagnosis and cure, which can be both inconvenient and costly. While millions seek the help of a physician for such problems, an even larger number (approximately 30% of all adult American women) often use douches purchased without a prescription, rather than seek medical advice.

The idea of washing out the foul smelling discharge with an acidic douche may have a simplistic appeal. Medically, however, douching is frowned upon as studies have demonstrated an association between douching and Pelvic Inflammatory Disease (PID), ectopic pregnancy, tubal infertility, and reduced fertility. Aral, S. O., et at., *Self-reported pelvic inflammatory disease in the United States, 1988, JAMA* 1991, 266:2570–3; Wolner-Hansen, P., et al., *Association between vaginal douching and acute pelvic inflammatory disease, JAMA* 1990, 263:1936–41; Scholes, D., et al., *Vaginal douching as a risk factor for acute pelvic inflammatory disease, Obstet. Gynecol.* 1993, 81:601–6; Chow, W-H, et al., *Vaginal douching as a riskfactor for tubal ectopic pregnancy, Am. J. Obstet.* 1985, 153:727–9; Chow, J. M., et al., *The association between Chlamydia trachomatis and ectopic pregnancy, JAMA* 1990, 263:3164–7; Darling J. R., et al., *Vaginal douching and the risk of tubal pregnancy*, Epidemiology 1991, 2:40–8; Kendrick, J. S., et al., *Vaginal douching and the risk of ectopic pregnancy among black women*, Am. J. Obstet. Gynecol. 1997, 176:991–7; Baird, D. D., et al., *Vaginal Douching and reduced fertility*, Am. J Public Health 1996, 86:844–50.

Traditional treatments of BV have focused on long-term cure. Treatment with the classic agents metronidazole and clindamycin have resulted in an approximately 70 percent cure rate within one month. Amsel, R., et al., *Nonspecific vaginitis. Diagnostic criteria and microbial and epidemiologic associations*, Am. J. Med 1983, 74:14–22; Larsson, P. G., *Treatment for bacterial vaginosis: an update on the expected cure rate*, Int'l J. of STD & AIDS 1997, 8:35–6. Nevertheless, only half of the women treated successfully will have a long-term cure. Larsson, P. G., et al., *Treatment of bacterial vaginosis in women with vaginal bleeding complications or discharge or harboring Mobiluncus*, Obstet. Gynecol. 1990, 29:296–300. Most relapses occur in the first year, often correlating to the introduction of a new sexual partner. Id. Thus, control of chronic BV is of primary importance to those who must deal with the problem.

SUMMARY OF INVENTION

The present invention relates to a pharmaceutical composition for preventing premature labor comprising a therapeutically-effective amount of aqueous pH-buffering bioadhesive water-insoluble but water-swellable cross-linked polycarboxylic acid polymer.

The present invention also relates to a pharmaceutical composition for preventing miscarriage comprising a therapeutically-effective amount of aqueous pH-buffering bioadhesive water-insoluble but water-swellable cross-linked polycarboxylic acid polymer.

The present invention also relates to a pharmaceutical composition for treating or preventing Bacterial Vaginosis comprising a therapeutically-effective amount of aqueous pH-buffering bioadhesive water-insoluble but water-swellable cross-linked polycarboxylic acid polymer.

The present invention further relates to a method of preventing premature labor, comprising administering a composition containing a therapeutically effective amount of an aqueous pH-buffering bioadhesive water-insoluble but water-swellable cross-linked polycarboxylic acid polymer to the vagina of a patient in need thereof.

The present invention further relates to a method of preventing miscarriage, comprising administering a composition containing a therapeutically effective amount of an aqueous pH-buffering bioadhesive water-insoluble but water-swellable cross-linked polycarboxylic acid polymer to the vagina of a patient in need thereof.

The present invention also relates to a method of treating or preventing Bacterial Vaginosis, comprising administering a composition containing a therapeutically effective amount of an aqueous pH-buffering bioadhesive water-insoluble but water-swellable cross-linked polycarboxylic acid polymer to the vagina of a patient in need thereof.

DETAILED DESCRIPTION OF THE INVENTION

Definitions

"Treating or preventing Bacterial Vaginosis" refers to:
(i) preventing Bacterial Vaginosis in females that may be predisposed to bacterial vaginosis;
(ii) inhibiting Bacterial Vaginosis, i.e., arresting its development; and/or
(iii) relieving Bacterial Vaginosis, i.e., causing its regression or the regression of symptoms associated with bacteria vaginosis.

"Preventing miscarriage" includes, without limitation, eliminating miscarriage, or reducing the incidences of miscarriage in women by treating or preventing Bacterial Vaginosis, whether or not the symptoms of Bacterial Vaginosis are manifest in the patient.

"Preventing premature labor" includes, without limitation, eliminating premature labor, or reducing the incidences of premature labor in women by treating or preventing Bacterial Vaginosis, whether or not the symptoms of Bacterial Vaginosis are manifest in the patient.

"Therapeutically effective amount" refers to the amount required to produce the desired medical result.

"Patient" refers to a person who is under medical care or treatment.

Pharmaceutical Composition of the Present Invention

The water-swellable but water-insoluble cross-linked bioadhesive polycarboxylic acid polymer formulation used in the present invention is generally described in U.S. Pat. No. 4,615,697 to Robinson (hereinafter "the '697 patent"), which is incorporated herein by reference. At least eighty percent of the monomers of which the polymer is comprised should contain at least one carboxyl functionality. The cross-linking agent must be present at such an amount as to provide sufficient bioadhesion and water insolubility. These characteristics allow the system to remain attached to the target epithelial surfaces for a sufficient time to effectively reduce the vaginal pH level. Generally, the polymer should be present in the formulation at about 0.5 to about 5 percent by weight, although as much as 8 percent by weight is acceptable. Preferably, the polymer is present in the invention at about 2 percent by weight.

A sufficient level of bioadhesion is usually attained when the cross-linking agent is present at about 0.1 to 6.0 weight percent of the polymer. More preferably, the cross-linking agent is present at about 1.0 to 2.0 weight percent of the polymer. Suitable cross-linking agents include, among others, divinyl glycol, divinylbenzene, N,N-diallylacrylamide, 3,4-dihydroxy-1,5-hexadiene, 2,5-dimethyl-1,5-hexadiene, and other similar agents. Adhesive strengths may be measured by commercially available surface tensiometers.

A preferred polymer for use herein is Polycarbophil. Polycarbophil U.S.P. is commercially available from B. F. Goodrich Specialty Polymers of Cleveland, OH, under the trade name NOVEON®-AA1. Polycarbophil is a polyacrylic acid that is cross-linked with divinyl glycol. *The United States Pharmacopeia*; 1995 edition, United States Pharmacopeial Convention, Inc., Rockville, Md., at pages 1240–41.

The instant polymer, and Polycarbophil in particular, has been used in a variety of drug delivery systems. The polymer formulation in the '697 patent is disclosed therein for use generally in a controlled release treatment composition, for providing controlled release of a separate treating agent. Specifically, the polymer has been disclosed for use in a controlled release composition with fluorometholone (U.S. Pat. No. 4,795,436) and with ophthalmic treatment compositions generally (U.S. Pats. Nos. 4,983,392 and 5,225,196). It has also been used in compositions to deliver other active treating agents, including, for example, progesterone (Crinone®) (see U.S. Pat. No. 5,543,150), Nonoxynol-9 (Advantage-S®) (see U.S. Pat. No. 5,667,492), and β-adrenergic agonists (see U.S. Pat. No. 6,126,959).

The polymer, and specifically Polycarbophil, is itself the active ingredient in the vaginal moisturizer Replens® (see U.S. Pat. No. 5,474,768 (vaginal moisturization). U.S. Pat. No. 5,968,500 also discloses use of the polymer for general epithelial tissue moisturization.

Use of the polymer to control vaginal pH to alleviate microorganism growth and feminine odor such as presented by bacterial vaginosis is disclosed in U.S. Pat. No. 6,017,521.

Other useful bioadhesive polymers that may be used in the inventive method are mentioned in the '697 patent. For example, these include polyacrylic acid polymers cross-linked with 3,4-dihydroxy-1,5-hexadiene, and polymethacrylic acid polymers cross-linked with divinyl benzene.

These polymers should not be used in their salt form because this would decrease their bioadhesive capability. These bioadhesive polymers may be prepared by conventional free radical polymerization techniques known to a skilled artisan, i.e., by utilizing initiators such as benzoyl peroxide and azobisisobutyronitrile. Exemplary methods of preparing useful bioadhesives are also disclosed in the '697 patent.

Additionally, any one or more of the additives or adjuvants taught in the '697 patent may be mixed in with the cross-linked polymer in the formulation for maximum efficacy of the pH buffering system or for the comfort of the patient. Such additives or adjuvants may include, among others, lubricants, plasticizing agents, preservatives, gel formers, tablet formers, pill formers, suppository formers, film formers, cream formers, disintegrating agents, coatings, binders, vehicles, coloring agents, taste controlling agents, odor controlling agents, humectants, viscosity controlling agents, and pH-adjusting agents. The present invention contemplates other additives known to an ordinarily skilled artisan.

The bioadhesive formulation may be in the form of a gel, cream, tablet, pill, capsule, suppository, film, or any other pharmaceutically acceptable form that adheres to the mucosa and does not wash away easily.

A preferred embodiment of the inventive composition comprises the following ingredients:

TABLE 1

Example of Preferred Embodiment

| INGREDIENT | AMOUNT (% w/w) |
| --- | --- |
| Purified Water | 83.900 |
| Glycerin | 12.900 |
| Polycarbophil | 2.000 |
| Carbomer 934P | 1.000 |
| Ethylmethylpropylparaben | 0.200 |

The individual ingredients of the preferred embodiment in Table 1 are well known and readily available from suppliers known in the industry.

Glycerin is a humectant. Alternative humectants include, for example, propylene glycol and dipropylene glycol.

Carbomer 934P is a gel former, which may be substituted by other gel formers including, but not limited to, carbomer 974, carbomer 980, methylcellulose or propylcellulose.

Ethylmethylpropylparaben is a preservative, which may be substituted by any other known preservative, such as benzoic acid or propionic acid.

The preferred embodiment of Table 1 may be generally prepared as follows. The ethylmethylpropylparaben (NIPASEPT®, Nipa Laboratories Ltd.) is completely dissolved in the purified water. The glycerin is then added to the water phase. After the glycerin is completely dissolved in the water phase, the polycarbophil ((NOVEON AA1®, B.F. Goodrich Specialty Polymers) and Carbomer 934P (CARBOPOL® 974P, B. F. Goodrich Chemical Co.) are added by very slowly vortex of the blender. The composition is mixed until the polymers have fully dispersed and the mixture is thoroughly homogenized. A vacuum of approximately −0.3 bar is then applied and the mixture is left for 20 minutes to allow for deaeration while mixing. The result is a uniform, creamy white product with a pH generally of about 3.

As will be apparent to those skilled in the art, the composition can be varied to affect certain properties of the formulation. For example, the concentration of the bioadhesive polymer can be adjusted to provide greater or lesser bioadhesion. The viscosity can also be varied by varying the pH or by changing the concentration of the polymer or gel former.

A second preferred embodiment of the inventive composition comprises the following ingredients:

TABLE 2

Second Example of Preferred Embodiment (Replens ®)

| INGREDIENT | AMOUNT (% w/w) |
| --- | --- |
| Purified Water | 78.82 |
| Glycerin | 12.90 |
| Polycarbophil | 2.00 |
| Mineral Oil | 4.20 |
| Carbomer 934P | 1.00 |
| Hydrogenated Palm Oil Glyceride | 1.00 |
| Sorbic Acid | 0.08 |

The individual ingredients of the preferred embodiment in Table 2 are well known and readily available from suppliers known in the industry.

Glycerin is a humectant. Alternative humectants include, for example, propylene glycol and dipropylene glycol.

Carbomer 934P is a gel former, which may be substituted by other gel formers including, but not limited to, Carbomer 974, Carbomer 980, methylcellulose or propylcellulose.

Mineral oil and hydrogenated palm oil glyceride are lubricating agents. Alternatives include, for example, any mineral oil or vegetable oil, such canola oil, palm oil or light mineral oil.

Sorbic acid is a preservative, which may be substituted by any other known preservative, such as benzoic acid or propionic acid.

General preparation involves hydration of the polymers, separate mixing of the polymer phase (water-soluble ingredients) and the oil phase (oil-soluble ingredients), heating and mixing of the two phases, and homogenization of the mixture. As an example, the polymer phase may be prepared by dissolving sorbic acid in purified water (which should contain approximately 3% of excess volume to account for evaporative losses), preferably at 75°–78° C. The mixture is then cooled generally to room temperature, and the polycarbophil and Carbomer 934P are added to the mixture. The polymers are hydrated by mixing for several hours, generally about 2–3 hours until a uniform, smooth, homogenous, lump-free, gel-like polymer mixture is obtained.

The oil phase is generally prepared by melting together the hydrogenated palm oil glyceride, glycerin, and mineral oil. The mixture is then cooled to about 60° C. The polymer phase, described above, is meanwhile warmed to about the same temperature. The polymer phase is then added to the heated oil phase. The two phases are mixed thoroughly, producing a uniform, creamy white product with a pH generally of about 3. When the mixture is cooled, it is de-aerated.

As will be apparent to those skilled in the art, the composition can be varied to affect certain properties of the formulation. For example, the concentration of the bioadhesive polymer can be adjusted to provide greater or lesser bioadhesion. The viscosity can also be varied by varying the pH or by changing the concentration of the polymer or gel former.

Methods of the Present Invention

The present inventive relates to methods and compositions for preventing miscarriage and premature labor and for treating or preventing Bacterial Vaginosis, comprising inclusion or use of a therapeutically effective amount of an aqueous pH-buffering bioadhesive water-insoluble but water-swellable cross-linked polycarboxylic polymer for vagina administration, thereby reducing vaginal pH for an extended period of time.

It is possible to reliably reduce vaginal pH for an extended period of time using a weak poly-acid containing multiple carboxyl radicals that are the source of its negative charges. These acid radicals permit hydrogen bonding with the cell surface. Although hydrogen bonds are weak, they are numerous and therefore tenacious. Robinson, J. R., Leung S-H, Park, H., *Mechanisms of adhesion of swelling insoluble polymers to mucin epithelial surfaces, Proceedings of the 12th International Symposium on Controlled Release of Bioactive Materials*, 12 (1985); Park, H., Rovinso, J. R., *Physico-chemical properties of water insoluble polymers important to mucinlepithelial adhesion, J. of Controlled Release* 2, 47–57 (1985). Thus, the bioadhesive polymers stay attached to the vaginal epithelial cells until they turnover, normally up to 3 to 5 days. Id., March, D., Nakamura, R., *Evaluation of the duration of effect of a bioadhesive vaginal moisturizing gel on vaginal pH, Abstract presented at the 7th International Congress on the Menopause*, Jun. 20–24, 1993, Stockholm, Sweden. Since the polymers are weak poly-acids with exceedingly high buffering capacity, they maintain the vaginal pH in the physiologic range of less than 5 and thus help protect against infection. Id. This effect has been shown to persist for more than 96 hours. Id. Polycarbophil, as an example, has a pKa of 4.3 and, as with all good buffers, it will adjust the pH of the environment close to its pKa. Vaginal douches, on the other hand, have only a transient effect upon vaginal pH and cannot maintain a physiologic pH.

Preferably the inventive formulation remains attached to the epithelial surfaces for a period of at least 24 to 48 hours. Such results may be measured clinically over various periods of time, by testing samples from the vagina for pH reduction due to the continued presence of the polymer.

The rationale for using a vaginal preparation containing such a bioadhesive polymer is its ability to maintain vaginal pH in the physiologic range, thereby preventing the volatilization of amines, favoring the restoration of acidophilic lactobacilli as the dominant member of the flora, and making the environment hostile to a profuse mixed facultative and anaerobic microbial flora.

EXAMPLES

The following examples are illustrative of the present invention and are not intended to be a limitation thereon.

Example 1

Evaluation of the Effects of Polycarbophil Gel on pH and Vaginal Flora in Women with Symptoms of Bacterial Vaginosis This was a randomized, single phase, parallel design study comparing the effects of Polycarbophil gel and Massengil® Vinegar and Water Douche on the vaginal pH level in women diagnosed with Bacterial Vaginosis. The objective of this study was to verify the therapeutic effects of Polycarbophil vaginal gel on the pH and vaginal flora in women with symptoms of Bacterial Vaginosis.

Forty-four women between the ages of 18 and 60 years and with a diagnosis of Bacterial Vaginosis completed the study. The diagnosis of Bacterial Vaginosis was made according to the following findings/symptoms: vaginal pH greater than 4.5 (evaluated using reactive strips), "clue cells" (3–4 cells per field) detected during the microscopic exam, and a fish-like vaginal odor with KOH (positive) test.

The study's participants were administered either 2.0 g of polycarbophil gel, prepared as described with respect to the preferred embodiment in Table 1, or Massengil® Vinegar and Water Douche twice a week for eight weeks. Polycarbophil gel contains Polycarbophil, a polymer whose high buffering capacity is able to acidify and stabilize vaginal pH. Massengil® Vinegar and Water Douche is an acidified vaginal douche.

The efficacy of the two treatments was evaluated by measuring vaginal pH and conducting a microbiological exam of vaginal secretions. Evaluation of the patients occurred at baseline, four weeks, and eight weeks. Vaginal pH was determined by performing an evaluation in the lateral vaginal formix. The microbial exam was performed four hours after the last gel or douche application, and the exams were performed at least seven days after the end of the last menstrual cycle and at least 24 hours after the last occurrence of sexual intercourse. After completion of the 8-week study, patients were asked to evaluate the acceptability of their assigned product and compare it to past use of vaginal creams, gels, and/or douches via a patient questionnaire.

At the end of eight weeks there was a statistically and clinically significant reduction in vaginal pH from a mean of 5.1 to 4.6 in the women who received Polycarbophil gel. There was a slight, but clinically insignificant, reduction of vaginal pH from 5.0 to 4.9 in the women who used the Massengil® douche. The results are displayed in Table 3.

TABLE 3

| Effect of Polycarbophil Gel on Vaginal pH | | | |
|---|---|---|---|
| | Baseline | Week 4 | Week 8 |
| Polycarbophil gel 2.0 g (n = 23) pH | 5.1 | 4.7 | 4.6 |
| Massengil ® Vinegar & Water Vaginal Douche (n = 21) pH | 5.0 | 5.0 | 4.9 |

The difference between the reduction in pH resulting from the Polycarbophil gel and Massengil® Vinegar and Water Vaginal Douche was statistically significant.

The results of the study indicate that using twice weekly a gel containing, for example, 2% Polycarbophil makes it possible to maintain the vaginal pH in the physiologic range of fewer than 5.0. The study indicates that the reduction in pH is both rapid and dramatic, and appears to decline further with time. Additionally, because of the high buffering capacity of such polymers, the level of the baseline vaginal pH does not diminish such polymers capacity to reduce vaginal pH to normal physiologic levels. Thus, the use of these polymer gels as follow-up therapy after successful treatment with the classic agents may prove to be an efficient way to help maintain normal vaginal pH levels, thus lowering the high recurrence rate of bacterial vaginosis and reestablishing a lactobacilli dominant flora.

Example 2
Reduction of Vaginal pH in Women with Breast Cancer After Treatment with a Bioadhesive Polycarbophil Gel The study was undertaken to determine whether patients who have a history of breast cancer and who may experience vaginal dryness, vaginal irritation, or dyspareunia will benefit from application of a nonhormonal polycarbophil moisturizing get. The study design was a single-center, open label, prospective study in women with a history of breast cancer. Twenty-five women who had been treated or were being treated for breast cancer were enrolled. Patients were instructed to insert the contents of one applicator, containing 2.5 g of polycarbophil gel, prepared as described with respect to the preferred embodiment in Table 2, into the vagina three times per week at night for 3 months, and were given the option to use an additional application before intercourse. The patients returned to the clinic on a monthly basis for four months. Assessment appointments were scheduled so that the gel would have been applied during the 24-hour period before the appointment. During each appointment, vaginal pH was measured using pH indicator strips (ColorpHast, E. Merck, Germany). Gelfand, M. M, Wendman, E., *Treating Vaginal Dryness in Breast Cancer Patients. Results of Applying a Polycarbophil Moisturizing Gel*, J. of Women's Health 1994, 3:427–434.

TABLE 4

Reduction of Vaginal pH in Women with Breast Cancer After Treatment with a Bioadhesive Polycarbophil Gel

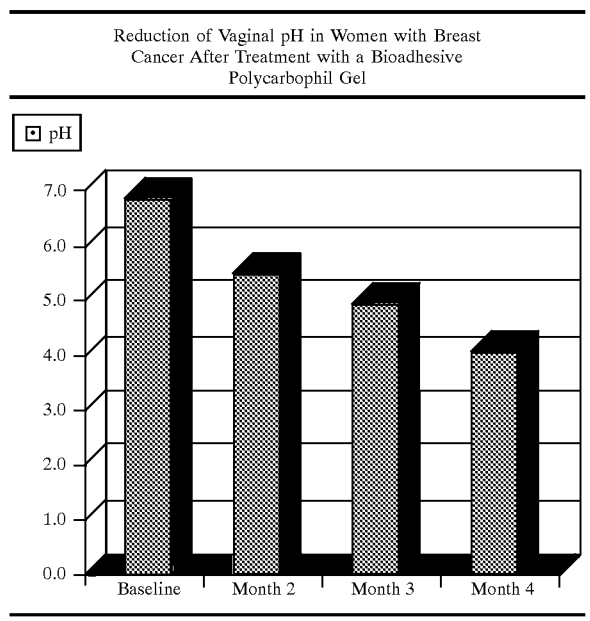

There was a statistically significant reduction in mean vaginal pH in the study population.

All twenty-five (25) patients who were originally enrolled completed the study. After month 1, the mean vaginal pH was 6.8, with a range of 5.8–8. 1. After month 4, the mean vaginal pH had decreased to 4.1, with a range of 3.0–4.7 (Table 4). Thus, it appears the polycarbophil gel with a pH of 3.0 effectively buffers to a normal vaginal pH of 3.5 to 5.0 in women with breast cancer. Id.

Example 3
Comparison of Effects of Polycarbophil Gel and Vaginal Douche on Vaginal pH in Women with Suspected Bacterial Vaginosis.

A randomized single center parallel design study comparing 2% Polycarbophil gel and the vaginal douche Lact-acid® was completed in thirty women with suspected Bacterial Vaginosis. The primary objective of the study was to determine the effect of 2% Polycarbophil gel and the vaginal douche on vaginal pH. The women were administered either 2.5 g of Polycarbophil gel, prepared as described with respect to the preferred embodiment in Table 1, or the vaginal douche Lactaid® twice a week for six weeks. The efficacy of both treatments was measured at baseline three and six weeks by using a Krison pH meter to measure the pH in the lateral vaginal formix. A microbiological exam was also performed to determine the presence or absence of clue cells and a whiff test with KOH to determine the presence of an amine odor.

At the end of six weeks there was a statistically and clinically significant reduction in vaginal pH from a mean of 5.4 to 4.6 in the fifteen women who received the 2% Polycarbophil gel. There was a slight, but clinically insignificant, reduction of vaginal pH from 5.6 to 5.3 in the fifteen women using the vaginal douche Lactaid®. The difference between the reduction in pH resulting from 2% Polycarbophil gel and Lactaid was statistically significant ($p<0.04$ two way ANOVA test).

Seven women in the 2% Polycarbophil gel group and four women in the vaginal douche group all had classic signs of Bacterial Vaginosis, including a pH above 4.7, clue cells, and a positive whiff test. At six weeks, the symptoms of Bacterial Vaginosis had disappeared in all but one of the women receiving 2% Polycarbophil gel. On the other hand, the vaginal douche did not significantly lower pH or eliminate clue cells. These results are displayed in Table 5.

TABLE 5

Effects of Polycarbophil gel and the Vaginal Douche on Symptoms of BV

|  | Baseline | Week 3 | Week 6 |
|---|---|---|---|
| Polycarbophil gel (n = 7) | | | |
| pH | 5.1 | 4.5 | 4.4 |
| Clue Cells | 7/7 | 1/7 | 1/7 |
| Whiff Test | 7/7 | 0/7 | 0/7 |
| Vaginal Douche (n = 4) | | | |
| pH | 5.7 | 5.5 | 5.4 |
| Clue Cells | 4/4 | ¾ | 4/4 |
| Whiff Test | 4/4 | ¾ | ¾ |

Any and all publications, patents, and patent applications mentioned in this specification are indicative of the level of skill of those skilled in the art to which this invention pertains. All publications, patents, and patent applications are herein incorporated by reference to the same extent as if each individual publication or patent application was specifically and individually indicated to be incorporated by reference.

Reasonable variations, such as those which would occur to a skilled artisan, can be made herein without departing from the spirit and scope of the invention.

We claim:

1. A pharmaceutical composition for preventing premature labor associated with bacterial vaginosis by buffering the vaginal pH, comprising a therapeutically-effective amount of an aqueous pH-buffering bioadhesive water-insoluble but water-swellable cross-linked polycarboxylic acid polymer, wherein said polymer provides said therapeutic effect regardless of whether any additional treating agent is present.

2. The composition of claim 1, wherein the polymer is polycarbophil.

3. The composition of claim 2, wherein the composition is a gel containing about 2% by weight polycarbophil.

4. The composition of claim 3, wherein the composition is formulated to provide a vaginal dose of about 2.0 to 2.5 g.

5. A pharmaceutical composition for preventing miscarriage associated with bacterial vaginosis by buffering the vaginal pH, comprising a therapeutically-effective amount of an aqueous pH-buffering bioadhesive water-insoluble but water-swellable cross-linked polycarboxylic acid polymer, wherein said polymer provides said therapeutic effect regardless of whether any additional treating agent is present.

6. The composition of claim 5, wherein the polymer is polycarbophil.

7. The composition of claim 6, wherein the composition contains about 2% by weight polycarbophil.

8. The composition of claim 7, wherein the composition is formulated to provide a vaginal dose of about 2.0 to 2.5 g.

9. A method of preventing premature labor associated with bacterial vaginosis by buffering the vaginal pH, comprising administering vaginally a composition containing a therapeutically-effective amount of an aqueous pH-buffering bioadhesive water-insoluble but water-swellable cross-linked polycarboxylic acid polymer to a patient in need thereof, wherein said polymer provides said therapeutic effect independent of any additional treating agent that may be present.

10. The method of claim 9, wherein the polymer is polycarbophil.

11. The method of claim 10, wherein the composition contains about 2% by weight polycarbophil.

12. The method of claim 11, wherein the composition is formulated to provide a vaginal dose of about 2.0 to 2.5 g.

13. The method of claim 12, wherein the composition is administered to the patient two to three times weekly.

14. A method of preventing miscarriage associated with bacterial vaginosis by buffering the vaginal pH, comprising administering vaginally a composition containing a therapeutically-effective amount of an aqueous pH-buffering bioadhesive water-insoluble but water-swellable cross-linked polycarboxylic acid polymer to a patient in need thereof, wherein said polymer provides said therapeutic effect independent of any additional treating agent that may be present.

15. The method of claim 14, wherein the polymer is polycarbophil.

16. The method of claim 15, wherein the composition is a gel containing about 2% by weight polycarbophil.

17. The method of claim 16, wherein the composition is formulated to provide a vaginal dose of about 2.0 to 2.5 g.

18. The method of claim 17, wherein the composition is administered to the patient two to three times weekly.

* * * * *

UNITED STATES PATENT AND TRADEMARK OFFICE
CERTIFICATE OF CORRECTION

PATENT NO. : 6,479,045 B2
DATED : November 12, 2002
INVENTOR(S) : Bologna et al.

It is certified that error appears in the above-identified patent and that said Letters Patent is hereby corrected as shown below:

Title page,
Item [56], References Cited, OTHER PUBLICATIONS, "Scholes, D., et al.," reference, change "Inflammaotory" to -- Inflammatory --.

Column 1,
Line 40, change "infections results" to -- infections: results --;
Line 44, change "333,1737-41" to -- 333:1737-42 --;
Line 45, change "*factorforpost-*" to -- *factor for post-* --;
Line 51, change "80, 173-77." to -- 80:173-77; --;
Line 66, change "*trimester. Cohort*" to -- *trimester: Cohort* --; and
Line 67, change "319,220-3" to -- 319:220-3 --.

Column 2,
Line 64, change "*riskfactor*" to -- *risk factor* --.

Column 6,
Line 2, change "slowly vortex" to -- slowly dispersing them into the vortex --; and
Line 41, change "such canola oil" to -- such as canola oil --.

Column 7,
Line 27, change "mucinlepithelial" to -- mucin/epithelial --.

Column 9,
Line 7, change "get" to -- gel --;
Line 23, change "*Patients. Results*" to -- *Patients: Results* --; and
Line 55, change "5.8-8. 1" to -- 5.8-8.1 --.

Signed and Sealed this

Fourteenth Day of October, 2003

JAMES E. ROGAN
*Director of the United States Patent and Trademark Office*